United States Patent [19]

Wolfe

[11] 4,208,325

[45] Jun. 17, 1980

[54] PREPARATION OF 1-OXAPENICILLINS AND 4-ACYLOXY AZETIDINONE INTERMEDIATES THEREFOR

[75] Inventor: Saul Wolfe, Kingston, Canada

[73] Assignee: Queen's University at Kingston, Kingston, Canada

[21] Appl. No.: 856,121

[22] Filed: Nov. 30, 1977

Related U.S. Application Data

[62] Division of Ser. No. 587,571, Jun. 17, 1975, Pat. No. 4,071,512.

[30] Foreign Application Priority Data

Jun. 19, 1974 [CA] Canada ................... 202890

[51] Int. Cl.² .................. C07D 205/08; C07D 403/12; C07D 409/12; C07D 407/12
[52] U.S. Cl. ............................. 260/239 A; 260/245.4; 260/347.3; 260/347.7; 260/347.4; 544/111; 544/359; 260/330.3
[58] Field of Search ................. 260/239 AL, 332.2 H, 260/347.3, 347.4, 347.2, 326.37, 293.69; 544/111, 359; 546/275

[56] References Cited

U.S. PATENT DOCUMENTS

| 3,948,927 | 4/1976 | Wolfe | 260/307 FA |
| 4,071,512 | 1/1978 | Wolfe | 260/268 C |

OTHER PUBLICATIONS

Wolfe et al. I, Can. J. Chem. 50, 2894–2897 (1972).
Brain et al., Chem. Abs. 84, 150420k.
Wolfe et al. II, Tetrahedron Letters 51, 5131–5134 (1973).
Stoodley et al., J. Chem. Soc. Perkins I, 1973, 32–35.
Lattrell, Annalen der Chemie 1974 (Sep.), pp. 1361, 1362, 1373, 1374.

Primary Examiner—Mark L. Berch
Attorney, Agent, or Firm—Omri M. Behr

[57] ABSTRACT

The invention provides a novel process for opening the ring of 2-R-6-(1'-R¹-oxycarbonyl-2'-methyl-prop-1'-enyl)-1-oxa-3,6-diaza-4$\underline{S}$,5$\underline{R}$-bicyclo[3,2,0]hept-2-en-7-one by treatment with a sulfonic acid salt thereby forming R¹ 2-(2'$\underline{R}$-R-oxy-3'$\underline{S}$-amino-4'-oxo)azetidinyl-3-methyl-2-butenoate sulfonic acid salts which can provide oxapenicillins by two different routes depending on the substituent desired on the carboxamido group of the 1-oxapenicillins. In the alternate processes, new intermediates are also provided.

2 Claims, No Drawings

PREPARATION OF 1-OXAPENICILLINS AND 4-ACYLOXY AZETIDINONE INTERMEDIATES THEREFOR

This is a division, of application Ser. No. 587,571, filed June 17, 1975, now U.S. Pat. No. 4,071,512, which was co-pending of application Ser. No. 496,620 filed Aug. 12, 1974, now U.S. Pat. No. 3,948,972 which in turn was a continuation of U.S. Ser. No. 242,842 filed Apr. 10, 1972.

The present invention relates to novel intermediates which are particularly useful in the preparation of 1-oxapenicillins and to a novel process for obtaining said novel intermediates.

PRIOR ART

The cyclization of a 2-(2'R-mercapto-3'S-acylamino-4'-oxo)azetidinyl-3-methyl-2-butenoic acid to a penicillin has been reported by S. Wolfe et al., J. Amer. Chem. Soc., Vol. 91, 1969, p. 7205.

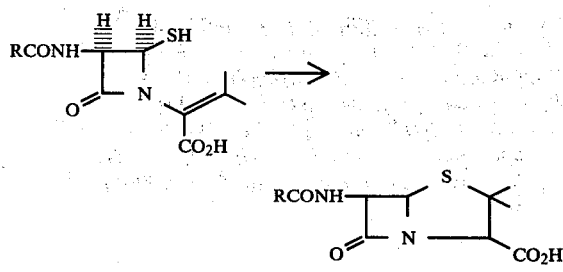

The formation of the thiazolidine ring proceeds by the Michael reaction as described in ORGANIC REACTIONS, Vol. 10 p. 179, and in Russian Chemical Reviews, Vol. 38, 1969, p. 884.

For the preparation of various 1-oxapenicillins of the general formula:

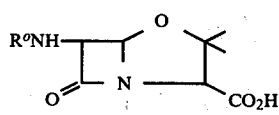

wherein $R^0$ is an acyl radical, it would be useful to have a procedure for the preparation of a 2-(2'R-hydroxy-3'S-acylamino-4'-oxo)azetidinyl-3-methyl-2-butenoic acid (the hydroxyl analog of the above-mentioned mercaptan), because the cyclization of this compound by the Michael reaction will generate the desired oxazolidine ring.

A potentially useful intermediate for the preparation of such a 2-(2'R-hydroxy-3'S-acylamino-4'-oxo)azetidinyl-3-methyl-2-butenoic acid is an oxazoline of the formula:

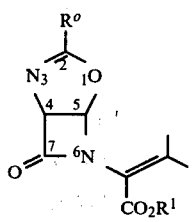

wherein $R^0$ and $R^1$ both stand for an organic radical. Such oxazolines have the correct oxidation level, functionality and absolute configurations at the 4- and 5-positions. Hydrolytic opening of the five-membered ring at the 1-2 bond would generate the desired alcohols but no simple procedure exists to effect the ring opening in this way. In some recent work by Corbet and Stoodley, J. Chem. Soc. Perkin I, 1974, p. 185, it is the 1-5 bond which breaks. In Canadian Pat. No. 1,024,518 issued Jan. 17, 1978, filed Mar. 22, 1973, corresponding to U.S. Pat. application Ser. No. 242,842, filed Apr. 10, 1972, now U.S. Pat. Nos. 3,948,927, 3,950,352, 3,985,764 S. Wolfe, inventor, the oxazolines have been converted directly into oxapenicillins by a procedure which requires rigorously anhydrous experimental conditions.

The oxazolines I ($R^0$=PhCH$_2$, PhOCH$_2$) are available directly from penicillin G or penicillin V by the methods of J. C. Sheehan, "Molecular Modification in Drug Design," Advances in Chemistry Series No. 45, American Chemical Society, Washington, D. C., 1964, p. 15; D. H. R. Barton et al, J. Chem. Soc. (C), 1971, p. 3540; and Stoodley and Whitehouse, J. Chem. Soc. Perkin I, 1974, p. 181. A general synthesis of oxazolines I from 2-(2'R-chloro-3'S-amino-4'-oxo)azetidinyl-3-methyl-2-butenoic acid is described in Canadian Pat. No. 1,024,518 issued Jan. 17, 1978 filed Mar. 22, 1973 corresponding to U.S. Pat. application Ser. No. 242,842, filed Apr. 10, 1972, now U.S. Pat Nos. 3,948,927, 3,950352, 3,985,764.

THE INVENTION

In accordance with the present invention there is now provided a method to open the ring of oxazolines of the general formula:

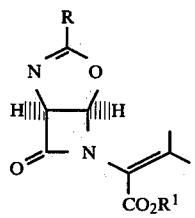

wherein
R stands for loweralkyl

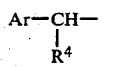

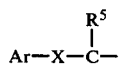

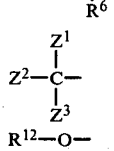

wherein
Ar is a monovalent radical selected from

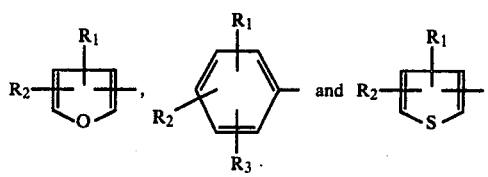

wherein
- $R_1$, $R_2$ and $R_3$ are each a member selected from hydrogen, chloro, bromo, iodo, trifluoromethyl, phenyl, loweralkyl and loweralkoxy, but only one of said $R_1$, $R_2$ and $R_3$ may represent phenyl;
- $R^4$ is hydrogen, amino, carbobenzoxyamino, phenyl, fluoro, chloro, bromo, iodo, hydroxy, loweralkanoyloxy and loweralkoxy;
- X is oxygen or sulfur;
- $R^5$ and $R^6$ are hydrogen, phenyl, benzyl, phenethyl and loweralkyl;
- $Z^1$, $Z^2$ and $Z^3$ stand for loweralkyl or the Ar- group;
- $R^{12}$ is 2,2,2-trichloroethyl or benzyl; and
- $R^1$ is loweralkyl, benzyl, benzhydryl, loweralkoxybenzyl, or 2,2,2-trichloroethyl.

Preferred values for R are loweralkyl, such as methyl or pentyl, phenoxymethyl, thienylmethyl and allylmercaptomethyl and preferred values for $R^1$ are methyl, benzyl, benzhydryl, methoxymethyl and all readily removable groups as will be hereinafter defined.

In accordance with the present invention, the ring in the oxazoline I, which is the 2-R-6-(1'$R^1$-oxycarbonyl-2'-methyl-prop-1'-enyl)-1-oxa-3,6-diaza-4S,5R-bicyclo[3,2,0]hept-2-en-7-one (I) may be readily opened to form the novel azetidinone sulfonic acid salt (II) by treatment with the monohydrate of a sulfonic acid. The ring opening may be illustrated as follows:

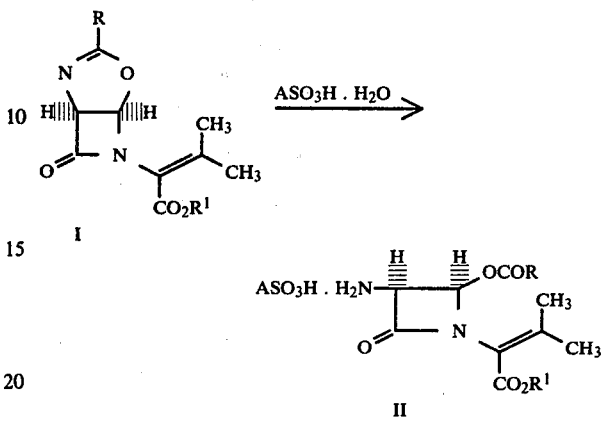

wherein A is the residue of a sulfonic acid.

As monohydrate of a sulfonic acid there may be used p-toluenesulfonic acid or benzenesulfonic acid or other sulfonic acids having an equivalent acidity.

The novel azetidinones II provide the advantage that they can then be readily converted to various 1-oxapenicillins in accordance with the following Flowsheet I:

FLOWSHEET I

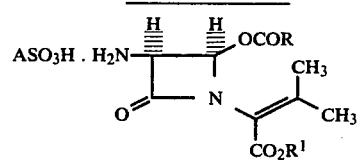

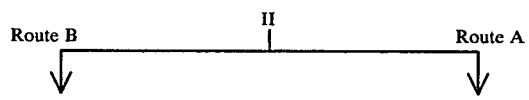

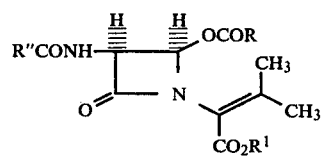

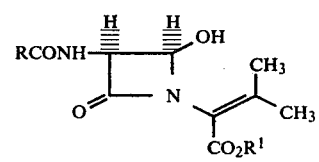

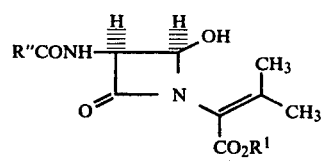

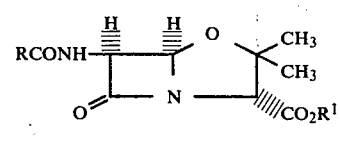

FLOWSHEET I

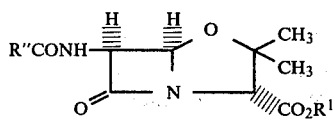

-continued

IIIA

As can be readily appreciated from the above reaction sequence the novel intermediates (II) of the present invention are useful to prepare 1-oxapenicillin by two different routes depending on whether it is desired to have the value of R in the 1-oxapenicillin the same as in the starting oxazoline I or different than in the oxazoline I.

1Oxapenicillin by Route A.

This route is conveniently used when it is desired that the value of R be the same in the 1-oxapenicillin as in the starting oxazoline I. In this sequence the sulfonic acid salt II is first neutralized to allow for rearrangement of the RCO-substituent from the 2'-position to the 3'-position. The neutralization step is carried out at room temperature or below in an aqueous organic solvent such as acetone, tetrahydrofuran, dimethylsulfoxide, N,N-dimethylformamide and the like or in a two phase system containing water and an immiscible organic solvent such as methylene chloride, chloroform, ether, benzene, ethyl acetate and the like over a period of at least thirty minutes thus forming the azetidinone IIA. Neutralization is carried out with any of the usual inorganic or organic bases. As an example of suitable inorganic bases there may be mentioned alkali metal carbonates or bicarbonates such as sodium or potassium carbonate or bicarbonate, and lithium carbonate; alkali metal hydroxides such as sodium or potassium hydroxides; alkaline earth carbonates such as strontium or calcium carbonate, and organic nitrogeneous bases such as the usual secondary or tertiary amines known to be useful as neutralizing agents such as diethylamine, triethylamine, diazabicyclononene or diazabicycloundecene. Preferably, when neutralizing with a strong base no more than one molar equivalent of such a base should be used. It should be appreciated that the critical feature of this step is that the reaction mixture should be allowed to stand until the RCO-group in the 2'-position of compound II has transferred to the 3'-position of compound IIA. Thus, for example in the mixture of water and chloroform containing 2 molar equivalents of triethylamine, the time required to transfer the RCO-group from the 2'-position to the 3'-position is at least 1½ hours when carrying out the reaction at room temperature.

Cyclization of the azetidinone IIA is carried out conveniently by the Michael addition procedure described by S. Wolfe in J.A.C.S. Vol. 91, p. 7205, 1969.

1-Oxapenicillin by Route B.

This route is conveniently used when it is desired to prepare a 1-oxapenicillin wherein the R group is different from the one present in the starting oxazoline I. For example, there may be situations where it is not feasible to have a certain substituent for R in the oxazoline I but these same substituents might be desirable in the 1-oxapenicillin.

As a first step, the sulfonic acid salt II is neutralized in an homogeneous or heterogeneous system and in the presence of an acid chloride of the formula R"COCl to form the azetidinone IIB.

As acylating agents there may be used an organic monocarboxylic acid chloride of the formula:

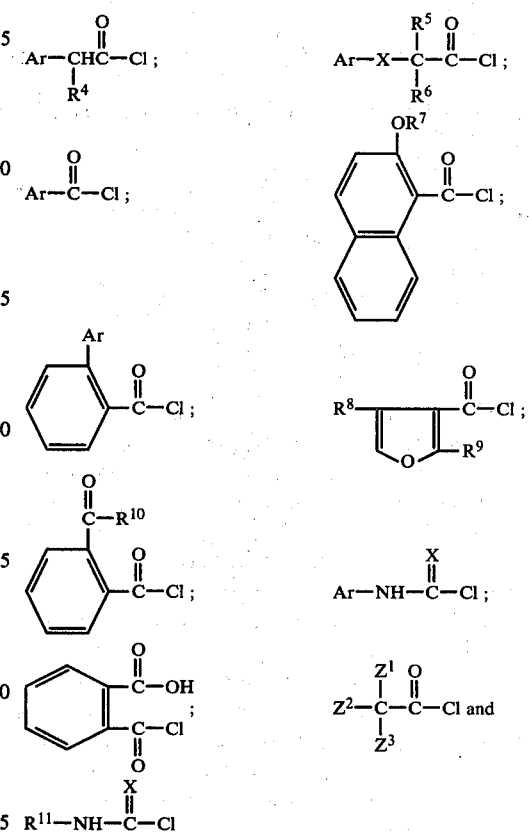

wherein $R^4$ represents a member selected from the group consisting of hydrogen, amino, carbobenzoxyamino, phenyl, fluoro, chloro, bromo, iodo, hydroxy, (lower)alkanoyloxy and (lower)-alkoxy; X represents a member selected from the group consisting of oxygen and sulfur; $R^5$ and $R^6$ each represent a member selected from the group consisting of hydrogen, phenyl, benzyl, phenethyl and (lower)alkyl; $R^7$ represents (lower)alkyl; $R^8$ and $R^9$ each represent a member selected from the group consisting of (lower)alkyl, (lower)alkylthio, benzylthio, cyclohexyl, cyclopentyl, cycloheptyl, benzyl, phenethyl, phenylpropyl, furyl, thienyl, naphthyl and Ar-; $R^{10}$ represents a member selected from the group consisting of (lower)alkylamino, di(lower)alkylamino, cycloalkylamino having from 3 to 7 carbon atoms inclusive, allylamino, diallylamino, phenyl(lower)alkylamino, morpholino, (lower)alkylmorpholino, di(lower)alkylmorpholino, morpholino(lower)alkylamino, pyrrolidino, (lower)alkylpyrrolidino, di(lower)alkylpyrrolidino, N,N-hexamethyleneimino, piperidino, (lower)alkylpiperidino, di(lower)-alkylpiperidino, 1,2,5,6-tetrahydropyridino, N-(lower)-alkylpiperazino, N-phenylpiperazino, N-(lower)alkyl(lower)-alkylpiperazino, N-(lower)alkyl-di(lower)alkylpiperazino, furfurylamino, tetrahydrofurfurylamino, N-(lower)alkyl-N-furfurylamino, N-alkyl-N-anilino and (lower)alkoxyanilino; $Z^1$, $Z^2$ and $Z^3$ each represent a member selected from the group consisting of (lower)alkyl and Ar-; $R^{11}$ represents a member selected from the group consisting of (lower)alkyl, (lower)-cycloalkyl, naphthyl, benzyl, phenethyl and

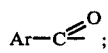

and Ar- represents a monovalent radical having one of the formulae:

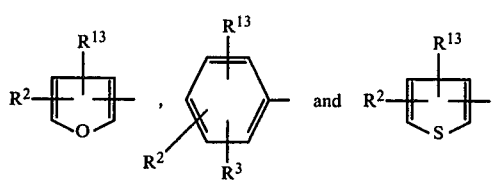

wherein $R^{13}$, $R^2$ and $R^3$ are each a member selected from the group consisting of hydrogen, chloro, bromo, iodo, trifluoromethyl, phenyl, (lower)alkyl and (lower)alkoxy, but only one R group may represent phenyl; or with a functional equivalent of said acid chloride.

The term "(lower)alkyl" as used herein means both straight and branched chain aliphatic hydrocrbon radicals having from one to ten carbon atoms such as methyl, ethyl, propyl, isopropyl, butyl, isobutyl, t-butyl, amyl, hexyl, 2-ethylhexyl, heptyl, decyl, etc. Similarly, where this term "(lower)" is used as part of the description of another group, e.g. "(lower)alkoxy," it refers to the alkyl portion of such group which is therefore as described above in connection with "(lower)alkyl."

The functional equivalents of the above acid chlorides as an acylating agent for a primary amino group include the corresponding carboxylic acid bromides, acid anhydrides, including mixed anhydrides and particularly the mixed anhydrides prepared from stronger acids such as the lower aliphatic monoesters of carbonic acid of alkyl and aryl sulfonic acids and of more hindered acids such as diphenylacetic acid. In addition, an acid azide or an active ester or thioester (e.g. with p-nitrophenol, 2,4-dinitrophenol, thiophenol, thioacetic acid) may be used or the free acid itself may be coupled with the primary amine after first reacting said free acid with N,N'-dimethylchloroforminium chloride [cf. Great Britain 1,008,170 and Novak and Weichet, Experientia XXI/6, 360 (1965) ] or by the use of enzymes or of an N,N'-carbonyldiimidazole or an N,N'-carbonylditriazole [cf. South African Patent Specification 63/2684], of a carbodiimide reagent [especially N,N'-dicychlohexylcarbodiimide, N,N'-diisopropylcarbodiimide or N-cyclohexyl-N'-(2-morpholinoethyl)-carbodiimide; cf. Sheehan and Hess. J. Amer. Chem. Soc. 77, 1067, (1955)], or of alkynylamine reagent; [cf. R. Buijle and H. G. Viehe, Angew. Chem. International Edition 3, 582 (1964) ], or of a ketenimine reagent [cf. C. L. Stevens and M. E. Monk, J. Amer. Chem. Soc. 80, 4065 (1–58)] or of an isoxazolium salt reagent [cf. R. B. Woodward, R. A. Olofson and H. Mayer, J. Amer. Chem. Soc. 83, 1010 (1961)]. Another equivalent of the acid chloride is a corresponding azolide, i.e. an amide of the corresponding acid whose amide nitrogen is a member of a quasiaromatic five-membered ring containing at least two nitrogen atoms, i.e. imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolides. The byproduct, imidazole, precipitates and may be separated and the imidazolide isolated but this is not essential. The methods for carrying out these reactions to produce a penicillin and the methods used to isolate the pencillins so-produced are well-known in the art.

Saponification of the azetidinone IIB will provide the azetidinone IIC. This step may be carried out using condition similar to those employed for the transformation of the sulfonic acid salt (II) to the azetidinone IIA.

Finally the azetidinone IIC is converted to the 1-oxapenicillin (IIIA) in the same manner as described in Route A.

The 1-oxapenicillin derivatives III and IIIA may readily be converted to the corresponding free acids by any of the known methods for converting esters to free acids.

An additional feature of the present invention is that the azetidinones II obtained herein can also be used to prepare novel bromo derivatives of 1-oxapenicillin XXVI corresponding to the following general formula:

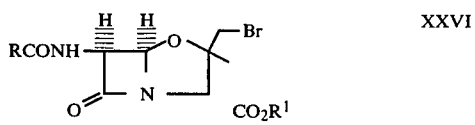

wherein R and $R^1$ are as previously defined.

These novel bromo deriviates of 1-oxapencillin XXVI may be prepared in accordance with the Flowsheet II:

FLOWSHEET II

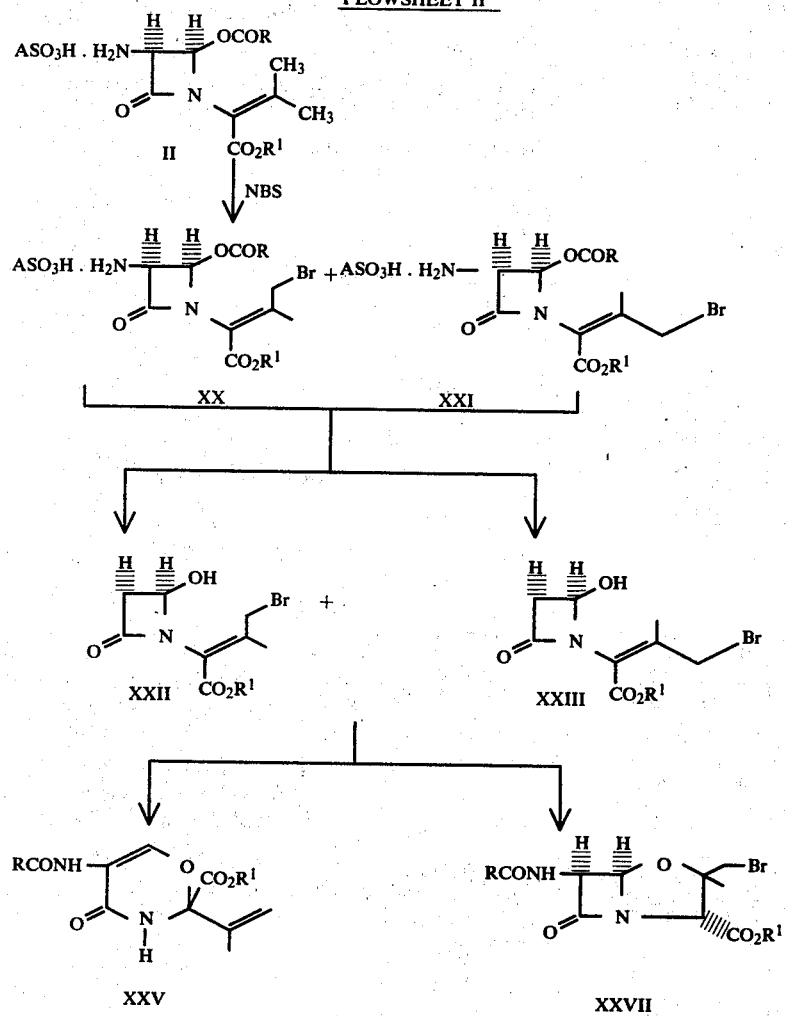

The novel bromo 1-oxapenicillins XXVI are prepared by first brominating the sulfonic acid salts II with at least one molar equivalent of N-bromosuccinimide in refluxing carbon tetrachloride or methylene chloride containing a catalytic amount of benzoyl peroxide in the presence of light thereby to form a mixture of the sulfonic acid salts XX and XXI.

This mixture of the azetidinones XX and XXI is then neutralized to allow rearrangement of the RCO-substituent from the 2'-position to the 3'-position. This neutralization step is carried out at room temperature or below in an aqueous organic solvent such as acetone, tetrahydrofuran, dimethylsulfoxide, N,N-dimethylformamide and the like or in a two phase system containing water and an immiscible organic solvent such as methylene chloride, chloroform, ether, benzene, ethyl acetate and the like to form the mixture of azetidinones XXII and XXIII. Neutralization is carried out with any of the usual inorganic or organic bases. As an example of suitable inorganic bases there may be mentioned alkali metal carbonates or bicarbonates such as sodium or potassium carbonate or bicarbonate, and lithium carbonate; alkali metal hydroxides such as sodium or potassium hydroxides; alkaline earth carbonates such as strontium or calcium carbonate, and organic nitrogeneous bases such as the usual secondary or tertiary amines known to be useful as neutralizing agents such as diethylamine, triethylamine, diazabicyclononene or diazabicycloundecene. Preferably when neutralizing with a strong base no more than one molar equivalent of such a base should be used.

Finally, the mixture of azetidinones XXII and XXIII may then either cyclize by the Michael addition procedure described in J.A.C.S. Vol. 91, p, 7205, 1969 to provide the novel brominated oxapenicillins XXVI, or undergo further rearrangement to the novel oxazinone derivatives XXV.;

EXAMPLE 1

Reaction of 2-benzyl-6-(1'-methoxycarbonyl-2'-methyl-prop-1'-enyl-1-oxa-3,6-diaza-4S,5R-bicyclo[3,2,0]hept-2-en-7-one with p-toluenesulfonic acid-monohydrate

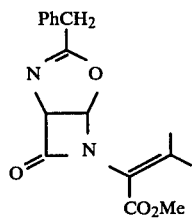

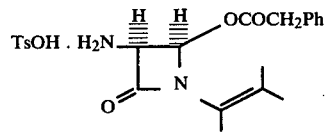

The 2-benzyl-6-(1'-methoxycarbonyl-2'-methyl-prop-1'-enyl-1-oxa-3,6-diaza-4S,5R-bicyclo[3,2,0]hept-2-en-7-one (500 mg, 1.6 mMoles) and p-toluenesulfonic acid monohydrate (300 mg, 1.6 mMoles) were stirred in dry acetone (20 ml) for 30 min. The solvent was then removed below 40° to give a colorless foam which was crystallized from acetonehexane to give 480 mg (60%) of methyl 2-(2'R-phenylacetoxy-3'S-amino-4'-oxo)azetidinyl-3-methyl-2-butenoate p-toluenesulfonate as colorless fine needles, after washing with cold ethyl acetate, m.p. 145°–146°, $[\alpha]_D^{EtOH}$ 40.1 (c 0.17).

Anal. Calcd. for $C_{24}H_{28}N_2O_8S$: C, 57.14; H, 5.56. Found: C, 56.75; H, 5.85.

The NMR spectrum has peaks at 7.83 (2H, d, 9 Hz), 7.06 (5H, s), 7.06 (2H, d, 9 Hz), 6.30 (1H, d, 4.0 Hz;), 4.90 (1H, d, 4.0 Hz), 3.62 (3H, s), 3.52 ;(2H, s), 2.30 (3H, s), 2.03 (3H, s), 1.88 (3H, s).

In KBr, the IR spectrum has peaks at 1800, 1776, 1728, 1699 $cm^{-1}$.

Proceeding in the same manner and replacing p-toluenesulfonic acid hydrate by benzenesulfonic acid hydrate there is obtained the corresponding benzenesulfonic acid salt having a m.p. 134° C.–135° C.

EXAMPLE 2

Proceeding in the same manner as above, but substituting for the 2-benzyl-6-(1'-methoxycarbonyl-2'-methylprop-1'-enyl)-1-oxa-3,6-diaza-4S,5R-bicyclo[3,2,0]hept-2-ene-7-one, the corresponding 2-phenoxymethyl, the 2-n-pentyl, the 2-(2-thienylmethyl), the 2-(3-thienylmethyl), and the 2-allyl-mercaptomethyl compounds, there are obtained the following salts:

1. methyl 2-(2'-R-phenoxyacetoxy-3'S-amino-4'-oxo)azetidinyl-3-methyl-2-butenoate p-toluenesulfonate;
2. methyl 2-(2'R-caproyloxy-3'S-amino-4'-oxo)azetidinyl-3-methyl-2-butenoate p-toluenesulfonate;
3. methyl 2-[2'R-(2-thienylacetoxy)-3'S-amino-4'-oxo-]azetidinyl-3-methyl-2-butenoate p-toluenesulfonate;
4. methyl 2-[2'R-(3-thienylacetoxy)-3'S-amino-4'-oxo]-azetidinyl-3-methyl-2-butenoate p-toluenesulfonate;
5. methyl 2-(2'R-allylthioacetoxy-3'S-amino-4'-oxo)azetidinyl-3-methyl-2-butenoate p-toluenesulfonate.

The reactions just named are:

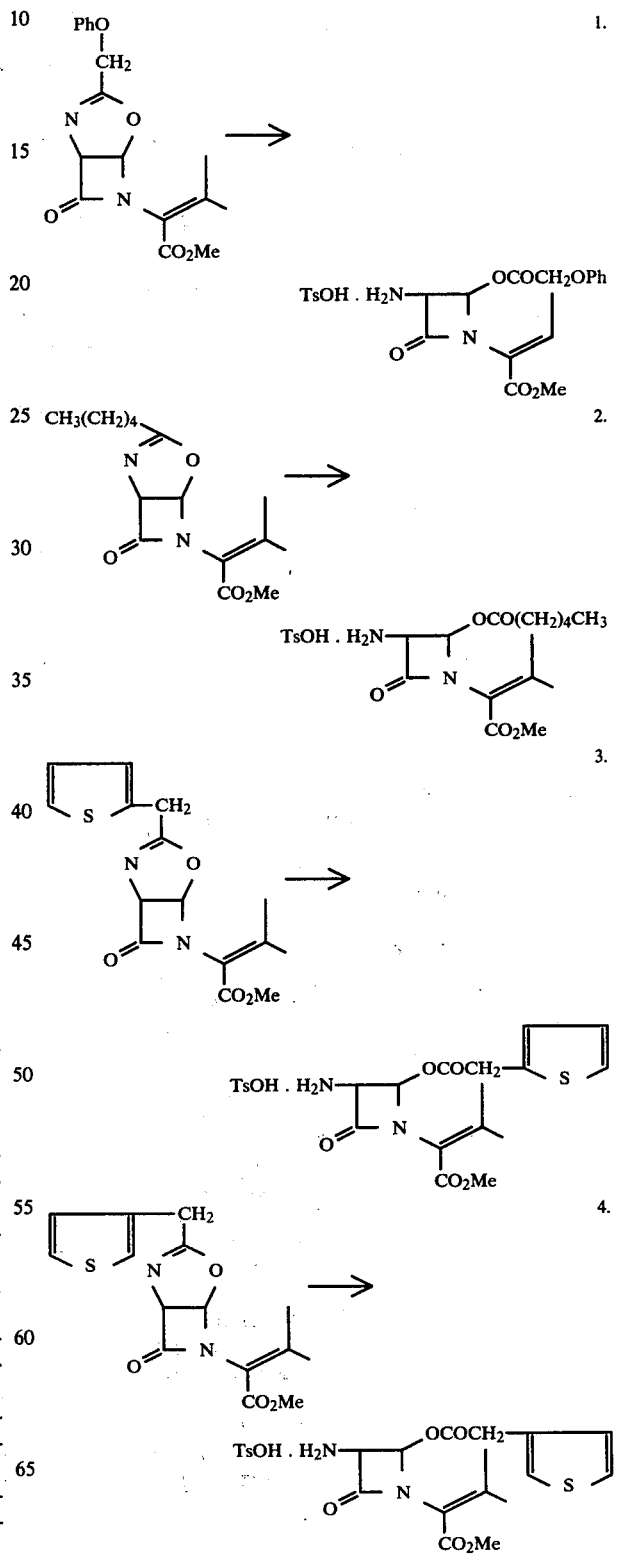

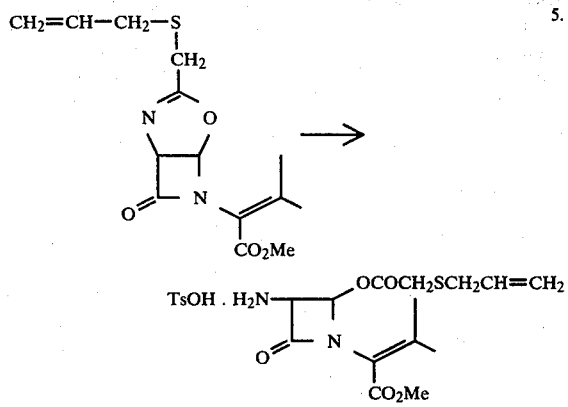

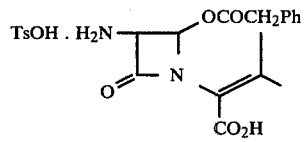

The NMR spectrum has peaks at 7.67 (2H, d, 8 Hz), 7.17 (5H, s), 7.00 (2H, d, 8 Hz), 6.35 (1H, d, 4 Hz), 4.97 (1H, d, 4 Hz), 3.47 (2H, s), 2.23 (3H, s), 2.00 (3H, s), 1.58 (3H, s).

EXAMPLE 4

Proceeding in the same manner as in Step A of Example 3, but substituting for the 2-benzyl-6-(1'-benzyloxycarbonyl-2'-methylprop-1'-enyl)-1-oxa-3,6-diaza-4S,5R-bicyclo[3,2,0]hept-2-en-7-one, the corresponding 2-phenoxymethyl, the 2-n-pentyl, the 2-(2-thienylmethyl), the 2-(3-thienylmethyl), and the 2-allylmercaptomethyl compounds, there are obtained the following salts:

1. benzyl 2-(2'R-phenoxyacetoxy-3'S-amino-4'-oxo)azetidinyl-3-methyl-2-butenoate p-toluenesulfonate;
2. benzyl 2-(2'R-caproyloxy-3'S-amino-4'-oxo)azetidinyl-3-methyl-2-butenoate p-toluenesulfonate;
3. benzyl 2-[2'R-(2-thienylacetoxy)-3'S-amino-4'-oxo]-azetidinyl-3-methyl-2-butenoate p-toluenesulfonate;
4. benzyl 2-[2'R-(3-thienylacetoxy)-3'S-amino-4'-oxo]-azetidinyl-3-methyl-2-butenoate p-toluenesulfonate;
5. benzyl 2-(2'R-allylthioacetoxy-3'S-amino-4'-oxo)azetidinyl-3-methyl-2-butenoate p-toluenesulfonate.

The reactions just named are:

EXAMPLE 3

Reaction of 2-benzyl-6-(1'-benzyloxycarbonyl-2'-methylprop-1'-enyl)-1-oxa-3,6-diaza-4S,5R-bicyclo[3,2,0]hept-2-ene-7-one with p-toluenesulfonic acid monohydrate

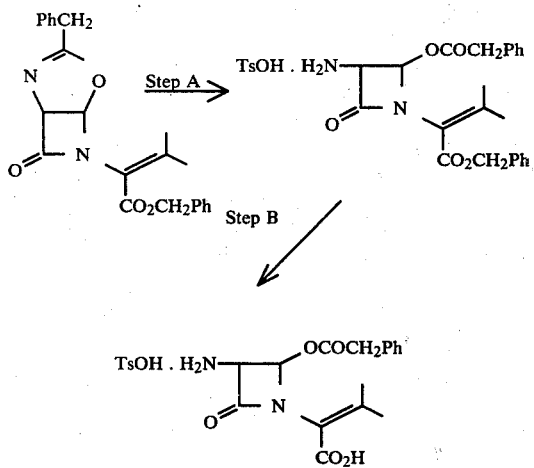

Step A:

The 2-benzyl-6-(1'-benzyloxycarbonyl-2'-methylprop-1'-enyl)-1-oxa-3,6-diaza-4S,5R-bicyclo[3,2,0]hept-2-ene-7-one (1.1 g, 2.8 mMoles) and p-toluenesulfonic acid monohydrate (532 mg, 2.8 mMoles) and p-toluenesulfonic acid monohydrate (532 mg, 2.8 mMoles) were stirred in dry acetone (50 ml) for 30 min. Removal of the solvent afforded a quantitative yield of benzyl 2-(2'R-phenylacetoxy-3'S-amino-4'-oxo)azetidinyl-3-methyl-2-butenoate p-toluenesulfonate, m.p. 128°–130° dec., after crystallization from ethyl acetate-petroleum ether.

The NMR spectrum has peaks at 7.68 (2H, d, 8 Hz), 7.15 (5H, s), 6.97 (5H, s), 6.93 (2H, d, 8 Hz), 6.23 (1H, d, 4Hz), 5.02 (s, 2H), 4.73 (br d, 4 Hz), 3.43 (2H, s), 2.23 (3H, s), 1.97 (3H, s), 1.50 (3H, s).

Step B:

The benzyl 2-(2'R-phenylacetoxy-3'S-amino-4'-oxo)azetidinyl-3-methyl-2-butenoate p-toluenesulfonate (100 mg) was hydrogenated at 15 psi in absolute ethanol (20 ml) containing 5% palladium on charcoal (10 mg) to give 2-(2'R-phenylacetoxy-3'S-amino-4'-oxo)azetidinyl-3-methyl-2-butenoic acid p-toluenesulfonate, having the structure:

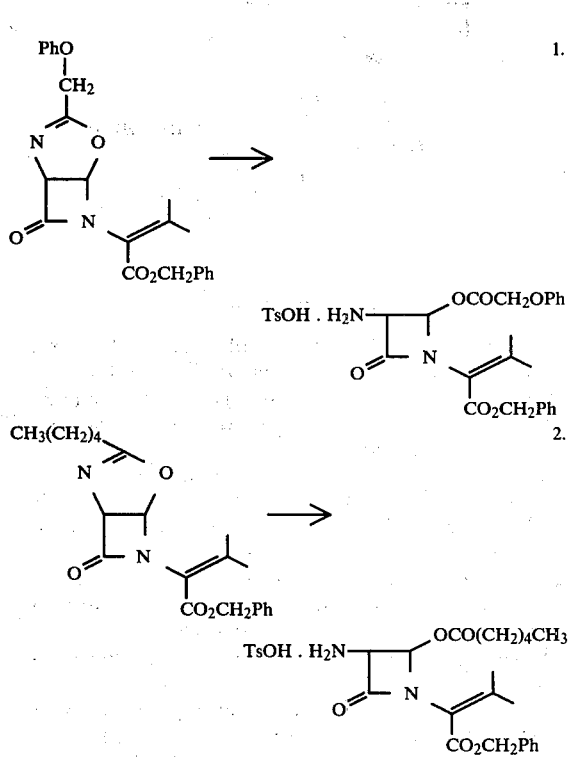

15
-continued

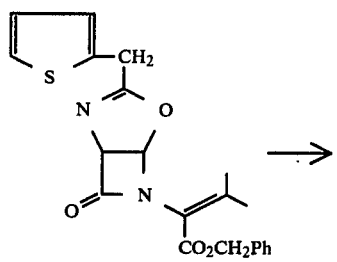

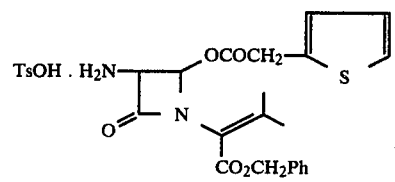

3.

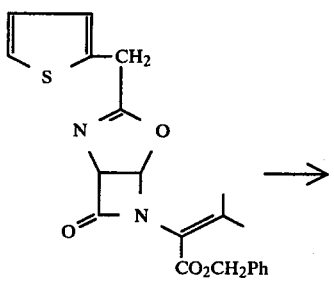

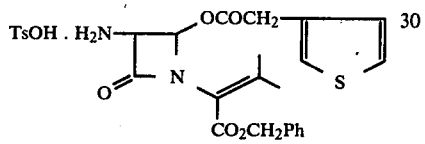

4.

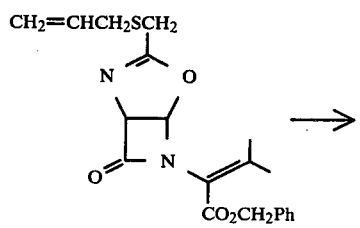

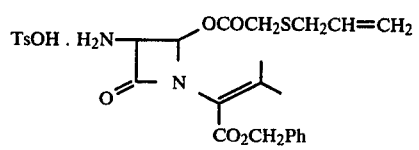

5.

EXAMPLE 5

In the same manner as Step B of Example 3, benzyl 2-(2'R-phenoxyacetoxy-3'S-amino-4'-oxo)azetidinyl-3-methyl-2-butenoate p-toluenesulfonate affords 2-(2'R-phenoxyacetoxy-3'S-amino-4'-oxo(azetidinyl-3-methyl-2-butenoic acid p-toluenesulfonate;

benzyl 2-(2'R-caproyloxy-3'S-amino-4'-oxo)azetidinyl-3-methyl-2-butenoate p-toluenesulfonate affords 2-(2'R-caproyloxy-3'S-amino-4'-oxo)azetidinyl-3-methyl-2-butenoic acid p-toluene-sulfonate;

benzyl 2-[2'R-(2-thienylacetoxy)-3'S-amino-4'-oxo]azetidinyl-3-methyl-2-butenoate p-toluenesulfonate affords 2-[2'R-(2-thienylacetoxy)-3'S-amino-4'-oxo]azetidinyl-3-methyl-2-butenoic acid p-toluenesulfonate;

benzyl 2-[2'R-(3-thienylacetoxy)-3'S-amino-4'-oxo]azetidinyl-3-methyl-2-butenoate p-toluenesulfonate affords 2-[2'R-(3-thienylacetoxy)-3'S-amino-4'-oxo]azetidinyl-3-methyl-2-butenoic acid p-toluenesulfonate;

benzyl 2-(2'-R-allylthioacetoxy-3'S-amino-4'-oxo)azetidinyl-3-methyl-2-butenoate p-toluenesulfonate affords 2-(2'R-allylthioacetoxy-3'S-amino-4'-oxo)azetidinyl-3-methyl-2-butenoic acid p-toluenesulfonate.

EXAMPLE 6

Conversion of Azetidinones II to Azetidinones IIB

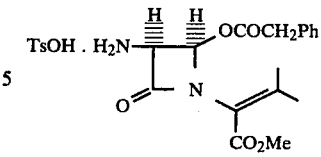

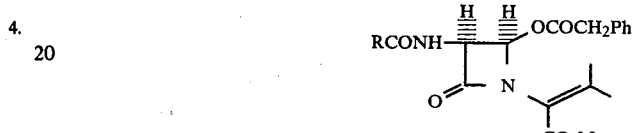

The benzyl 2-(2'R-phenylacetoxy-3'S-amino-4'-oxo)-azetidinyl-3-methyl-2-butenoate p-toluenesulfonate obtained in Example 1 (500 mg, 1.0 mMole) in $CH_2Cl_2$ (40 ml), cooled to 0°, was shaken vigorously for 30 min in an ice-bath with an ice cold solution of sodium bicarbonate (263 mg, 3.0 mMoles) in water (20 ml). Then a solution of benzoyl chloride (280 mg, 2.0 mMoles) in $CH_2Cl_1$ (10 ml) was added dropwise during 5 min and stirring continued at 0° for an additional 2 hr. The layers were then separted and the aqueous layer extracted twice with $CH_2Cl_2$. Evaporation of the combined dried $CH_2Cl_2$ layers afforded 550 mg of a colorless solid. Recrystallization from $CH_2Cl_2$-petroleum ether gave 330 mg (75.5%) of methyl 2-(2'R-phenylacetoxy-3'S-benzoylamino-4'-oxo)azetidinyl-3-methyl-2-butenoate ($R=C_6H_5$) as colorless prisms, m.p. 139°–141°.

The IR spectrum (KBr) has peaks at 1777, 1722, 1669 cm$^{-1}$.

The NMR spectrum has peaks at 7.78–6.97 (6H, m), 7.13 (5H, s), 6.37 (1H, d, 4 Hz), 5.58 (1H, 9, 2, 8 Hz), 3.73 (3H, s), 3.57 (2H, s), 2.18 (3H, s), 1.83 (3H, s).

To prove the structure of this compound, 2-benzyl-6-(1'-methoxycarbonyl-2'-methylprop-1'-enyl)-1-oxa-3,6-diaza-4S,5R-bicyclo[3,2,0]hept-2-en-7-one (the methyl ester of the oxazoline) was converted directly into the same material. The oxazoline (100 mg, 0.3 mMole) and benzoyl chloride (140 mg, 1 mMole) were stirred in THF (5 ml) at room temperature for 24 hr. Then water (2 ml) and $NaHCO_3$ (100 mg, 1.2 mMole) were added, and stirring continued for a further 30 min. The mixture was then diluted with water and extracted with $CH_2Cl_2$. After drying of this extract, evaporation yielded 140 mg of a yellow oil, whose NMR spectrum showed it to be a mixture of oxazoline and the above-mentioned N-benzoyl compound. This latter material was isolated by p.l.c. on silica gel (elution with 1:2 ethyl acetate:hexane) and crystallized from ethyl acetate-hexane. Its IR, NMR spectra, m.p. and mixture melting point with the N-benzoyl compound showed the two to be identical.

The meaning of this experiment is that benzoylation of the oxazoline must occur on nitrogen (E. M. Fry, J. Org. Chem., 15, 802 (1950)). In the formation of the diacylated azetidinone from the salt no O→N acyl transfer has, therefore, occurred.

In a second experiment, the salt was converted into the N-phenylacetyl compound by exactly the same procedure, except that acylation of the free amine was performed with phenylacetyl chloride. The structure of this latter compound is

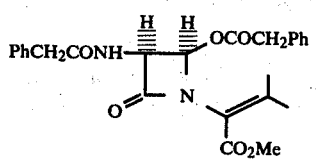

This compound has IR absorption at 2.9, 3.0, 5.60, 5.70, 5.80, 5.98, 6.05, 6.65μ. The NMR spectrum has peaks at 2.65-2.75 (10H, m), 3.26 (1H, d, 9.5 Hz), 3.68 (1H, d, 4.1 Hz), 4.53 (q, 4.1, 9.5 Hz), 6.27 (3H), 6.43 (2H), 6.54 (2H), 7.82 (3H), 8.28 (3H). The mass spectrum shows a molecular ion at m/e 450.

EXAMPLE 7

Acylation of Azetidinones II to Azetidinones IIB

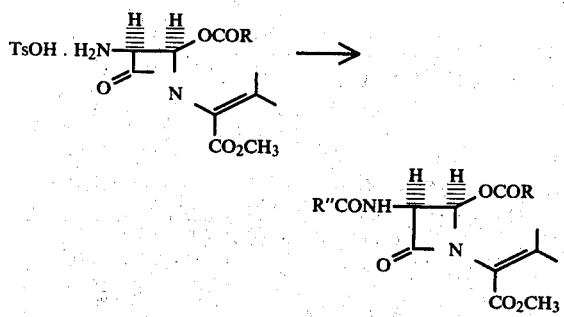

By proceeding in the same manner as in Example 6 and replacing the benzoyl chloride with α-aminophenylacetyl chloride, α-hydroxyphenylacetyl chloride, tetrazyl-1-yl-acetyl chloride, thiophen-2-yl-acetyl chloride, (3-phenyl-5-methylisoxazol-4-yl)acetyl chloride or α-carboxy-phenylacetyl chloride there is obtained the corresponding methyl 2-(2'R-phenylacetoxy-3'S-α-aminophenylacetamido-4'-oxo)azetidinyl-3-methyl-2-butenoate, methyl 2-(2'R-phenylacetoxy-α-hydroxyphenylacetamido-4'-oxo)azetidinyl-3-methyl-2-butenoate, methyl 2-(2'R-phenylacetoxy-3'S-tetrazyl-1-yl-acetamido-4'-oxo)-azetidinyl-3-methyl-2-butenoate, methyl 2-(2'R-phenylacetoxy-3'S-thiophen-2-yl-acetamido-4'-oxo)azetidinyl-3-methyl-2-butenoate, methyl 2-(2'R-phenylacetoxy-3'S-[3-phenyl-5-methylisoxazol-4-yl]acetamido-4'-oxo)azetidinyl-3-methyl-2-butenoate and methyl 2-(2'R-phenylacetoxy-3'S-α-carboxyphenylacetamido-4'-oxo)azetidinyl-3-methyl-2-butenoate which upon treatment in accordance with the following Examples will yield the 6-D(α)-aminophenylacetamido-oxapenicillanic acid, 6-D(α)hydroxyphenylacetamido-oxapenicillanic acid, 6-tetrazyl-1-yl-acetamidooxapenicillanic acid, 6-thiophen-2-yl-acetamido-oxapenicillanic acid, 6-[3-phenyl-5-methylisoxazol-4-yl]acetamidooxapenicillanic acid, and 6[D](α)carboxy-phenylacetamidooxapenicillanic acid.

EXAMPLE 8

Conversion of 2-(2'R-phenylacetoxy-3'S-phenylacetamido-4'-oxo)-azetidinyl-3-methyl-2-butenoic acid to 2,2-dimethyl-3R-carboxy-6S-phenylacetamido-1-oxa-4-aza-5R-bicyclo[3,2,0]heptan-7-one via 2-(2'R-hydroxy-3'S-phenylacetamido-4'-oxo)azetidinyl-3-methyl-2-butenoic acid

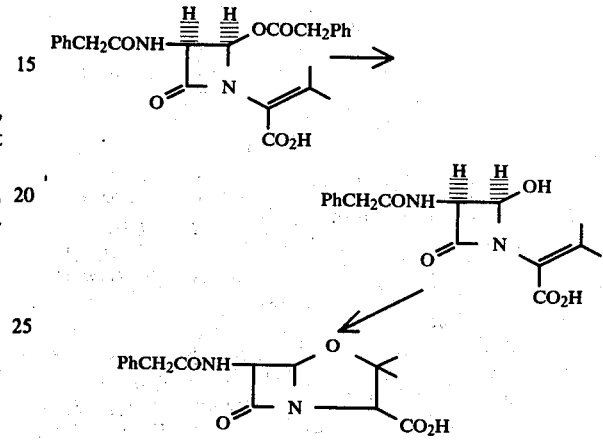

Forty-five milligrams of 2-(2'R-phenylacetoxy-3'S-phenylacetamido-4'-oxo)azetidinyl-3-methyl-2-butenoic acid are dissolved in ice-cold 0.05N methanolic sodium methoxide (4 ml). The solution containing the 2-(2'R-hydroxy-3'S-phenylacetamido-4'-oxo)azetidinyl-3-methyl-2-butenoic acid is stirred at 0°for 2 hr, and is then neutralized with ice-cold dilute HCl and extracted with ether. Evaporation of the dried ether extract yields 30 mg of material, which is found to contain phenylacetic acid and 2-(2'R-hydroxy-3'S-phenylacetamido-4'-oxo)-azetidinyl-3-methyl-2-butenoic acid. This material is dissolved in water (0.5 ml) containing sodium bicarbonate (42 mg) and after 3 hr, a 5 μl aliquot is allowed to evaporate upon a 1 cm-diameter filter paper. This is introduced onto an agar plate seeded with *S. lutea*, and the plate is allowed to develop overnight at 37°. A zone of inhibition, attributed to the presence of oxapenicillin G, is then observed. (cf. S. Wolfe et al, *J. Amer. Chem. Soc.*, 91, 7205 (1969)).

EXAMPLE 9

Conversion of Methyl 2-(2'R-phenylacetoxy-3'S-amino-4'-oxo)-azetidinyl-3-methyl-2-butenoate p-toluenesulfonate to Methyl 2-(2'R-hydroxy-3'S-phenylacetamido-4'-oxo)azetidinyl-3-methyl-2-butenoate and Cyclization to the Methyl Ester of Oxapenicillin G

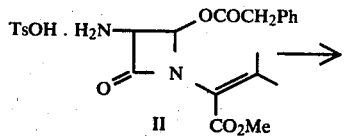

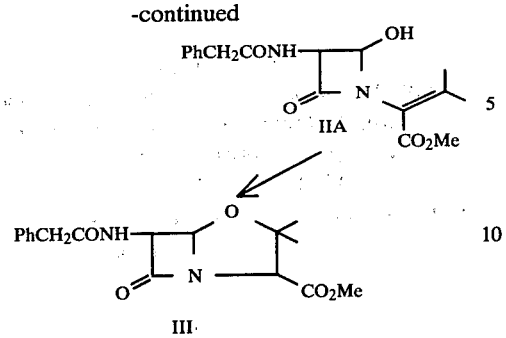

A solution of Methyl 2-(2'R-phenylacetoxy-3'S-amino-4'-oxo)azetidinyl-3-methyl-2-butenoate p-toluenesulfonate (II) in CDCl₃ is treated with two molar-equivalents of triethylamine, and the IR spectrum of the resulting solution is monitored as a function of time. After 2 min, the spectrum of methyl 2-(2'R-phenylacetoxy-3'S-amino-4'-oxo)azetidinyl-3-methyl-2-butenoate shows peaks at 5.60, 5.65 and 5.78µ, corresponding to the β-lactam, the phenylacetoxy and the carbomethoxy carbonyl groups. During the next 1.5 hr, the β-lactam absorption remains, but the phenylacetoxy absorption at 5.65µ disappears and phenylacetamido absorption appears at 5.98µ, corresponding to the O→N acyl transfer which forms the methyl 2-(2'R-hydroxy-3'S-phenylacetamido-4'-oxo)azetidinyl-3-methyl-2-butenoate.

Alternatively, the p-toluenesulfonic acid salt (II) (47 mg, 0.093 mMole) is dissolved in DMSO-d₆ (1 ml), TMS is added, and the NMR spectrum is recorded. This spectrum shows the 3'-proton as a doublet (4 Hz) at 5.08, the 4'-proton as a doublet (4 Hz) at 6.38, the CH₂ protons at 3.74, the methyl ester protons at 3.67, the methyl protons of the p-toluene-sulfonate ion at 2.28, and the gem-dimethyl protons at 2.10 and 1.82. A solution of K₂CO₃ (6.4 mg. 0.047 mMole) in D₂O (0.2 ml) is now added, and the NMR spectrum of the resulting solution is secured at intervals during a period of 26 hr. The 3'-proton becomes a quartet (J=4, 12 Hz) at 6.27, the 4'-proton becomes a doublet (J=4 Hz) at 5.00, the CH₂ protons shift upfield to 3.60, and the gem-dimethyl protons shift upfield to 2.00 and 1.72. The reaction mixture is then diluted with water and extracted with chloroform. The dried chloroform extract is concentrated and its IR spectrum recorded. This shows OH and NH absorption at 2.90 and 2.94µβ-lactam absorption at 5.60µ, conjugated ester at 5.81µ, and amide absorption at 6.02µ, corresponding to the formation of the compound methyl 2-(2'R-hydroxy-3'S-phenylacetamido-4'-oxo)-azetidinyl-3-methyl-2-butenoate.

This compound is cyclized to the methyl ester of 1-oxapenicillin G by the procedure of Example 8.

EXAMPLE 10

Removal of the phenylacetyl group from methyl 2-(2'R-phenylacetoxy-3'S-benzoylamino-4'-oxo)azetidinyl-3-methyl-2-butenoate

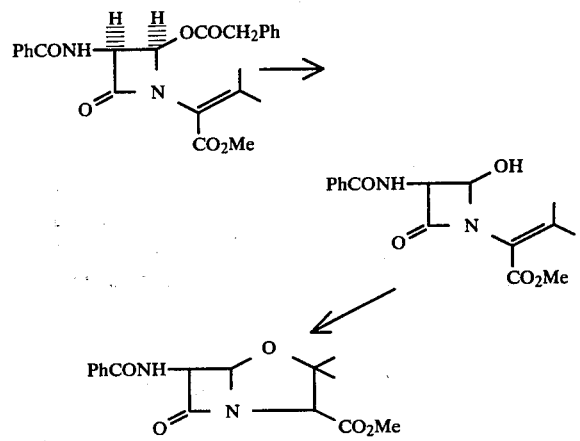

The methyl 2-(2'R-phenylacetoxy-3'S-benzoylamino-4'-oxo)azetidinyl-3-methyl-2-butenoate (100 mg) is dissolved in absolute ethanol (1 ml) containing pyridine (0.5 ml). This solution is cooled to 0° and then an additional 0.5 ml of ethanol is added, followed by 2N sodium hydroxide (0.5 ml). The mixture is stirred at 0° for 5 min, and is then acidified with ice-cold dilute HCl. Extraction with methylene chloride and evaporation of the dried organic layer affords phenylacetic acid and methyl 2-(2'R-hydroxy-3'S-benzoylamino-4'-oxo)azetidinyl-3-methyl-2-butenoate.

This compound is then cyclized to 2,2-dimethyl-3R-methoxycarbonyl-6S-benzoylamino-1-oxa-4-aza-5R-bicyclo[3,2,0]-heptan-7-one by the procedure of Example 8.

EXAMPLE 11

Conversion of methyl 2-(2'R-phenylacetoxy-3'S-amino-4'-oxo)-azetidinyl-3-methyl-2-butenoate p-toluenesulfonate to 2-isopropenyl-2-methoxycarbonyl-5-phenylacetamido-5,6-dehydrooxazine-4-one and the epimeric 2-bromomethyl-2-methyl-3R-methoxycarbonyl-6S-phenylacetamido-1-oxa-4-aza-5R-bicyclo[3,2,0]heptan-7-ones

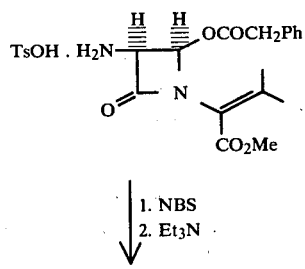

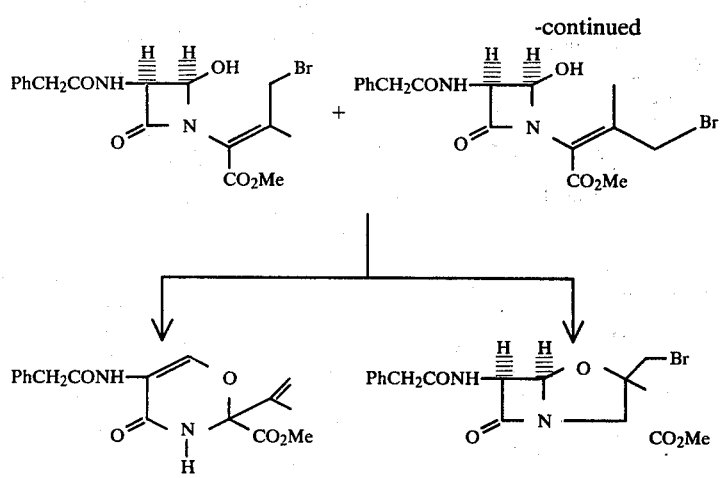

The methyl 3-(2'R-phenylacetoxy-3'S-amino-4'-oxo)azetidinyl-3-methyl-2-butenoate p-toluenesulfonate (504 mg, 1 mMole) was brominated for 15 min in CCl$_4$ (50 ml) with N-bromosuccinimide (356 mg, 2 mMoles to yield a mixture of the methyl 2-(2'R-phenylacetoxy-3'S-amino-4'-oxo)azetidinyl-3-methyl-trans-2-butenoate p-toluenesulfonate XX and corresponding cis-4-bromo isomer XXI. This mixture was dissolved in CH$_2$Cl$_2$ (30 ml) containing triethylamine (202 mg. 2 mMoles) to form the mixture of methyl 2-(2'R-hydroxy-3'S-phenylacetamido-4'-oxo)azetidinyl-3-methyl-trans-4-bromo-2-butanoate and methyl 2-(2'R-hydroxy-3'S-phenylacetamido-4'-oxo)azetidinyl-3-methyl-cis-4-bromo-2-butenoate and this solution was stirred at room temperature for 1 hr and then evaporated to dryness. The residue was triturated with methylene chloride and water and the dried methylene chloride phase was evaporated to give 310 mg of a white foam. Crystalline material m.p. 151°–152° C. was obtained as follows. The crude product was chromatographed on silica gel and eluted with 1:1 petroleum ether:ethyl acetate. Crystallization from petroleum ether-CH$_2$Cl$_2$ afforded 210 mg of the 2-isopropenyl-2-methoxycarbonyl-5-phenylacetamido-5,6-dehydrooxazine-4-one. Calcd. for C$_{17}$H$_{18}$N$_2$O$_5$ (M+1) 330.1205. Found: 330.1216.

The NMR spectrum has peaks at 8.04 (1H, s), 7.30 (5H, s), 5.24 (2H, d), 3.74 (3H, s), 3.66 (2H, s), 1.81 (3H, s) at 100 MHz in DMSO-d$_6$ containing a drop of D$_2$O.

The 2-isopropyl-2-methoxycarbonyl-5-phenylacetamido-5,6-dehydrooxazine-4-one upon hydrogenation in ethanol over 5% palladium on charcoal provided the dihydro derivative, melting point 178°–180°, having the following structure:

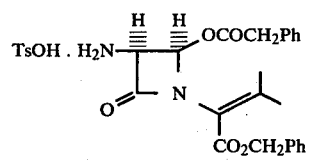

Its NMR spectrum shows the following peaks: 8.28 (1H, s), 7.38 (1H), 7.23 (5H), 7.18 (1H), 3.76 (3H), 3.63 (2H), 2.24 (1H, m), 1.00 (3H, d, 7 Hz), 0.94 (3H, d, 7 Hz).

The formation of 2-isopropenyl-2-methoxycarbonyl-5-phenylacetamido-5,6-dehydrooxazine-4-one in the reaction with triethylamine requires the intervention of methyl 2-(2'R-hydroxy-3'S-phenylacetamido-4'-oxo)azetidinyl-3-methyl-trans-4-bromo-2-butenoate and methyl 2-(2'R-hydroxy-3'S-phenylacetamido-4'-oxo)azetidinyl-3-methyl-cis-4-bromo-2-butenoate. These compounds can be cyclized by the procedure of Example 8 to the epimeric 2-bromomethyl-2-methyl-3R-methoxycarbonyl-6S-phenylacetamido-1-oxa-4-aza-5R-bicyclo-[3,2,0]heptan-7-ones.

EXAMPLE 12

Conversion of benzyl 2-(2'R-phenylacetoxy-3'S-amino-4'-oxo)-azetidinyl-3-methyl-2-butenoate p-toluenesulfonate to 2-isopropenyl-2-benzyloxycarbonyl-5-phenylacetamido-5,6-dehydrooxazine-4-one and the epimeric 2-bromomethyl-2-methyl-3R-benzyloxycarbonyl-6S-phenylacetamido-1-oxa-4-aza-5R-bicyclo[3,2,0]heptan-7-ones

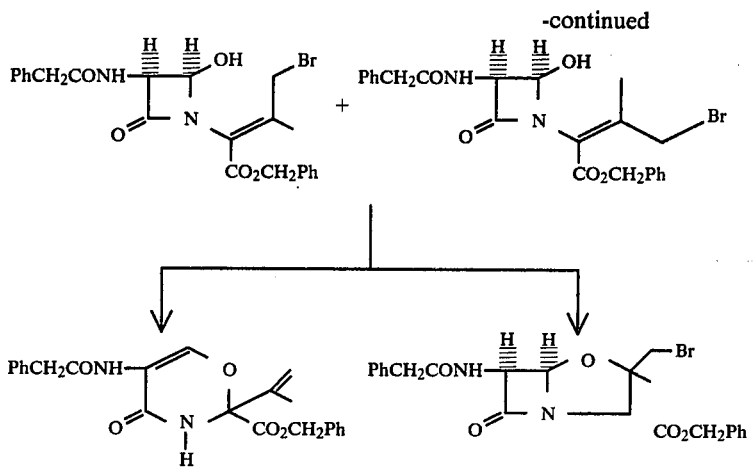

The p-toluenesulfonic acid salt (100 mg, 0.17 mMole) was suspended in CCl$_4$ (spectroscopic grade, 20 ml) containing N-bromosuccinimide (62 mg, 0.35 mMole) and benzoyl peroxide (2mg). The mixture was heated to reflux with mechanical stirring. After 2 min, the heat source was removed, and the stirred mixture was irradiated with a 100 watt Photoflood No. 2 lamp for 8 min. Irradiation was then discontinued, and the reaction mixture was evaporated to dryness to form the mixture XX and XXI where R=R'=benzyl and A=p-tolyl. The residue was dissolved in methylene chloride (15 ml) and triethylamine (35 mg) was added to form the mixture XXII and XXIII where R=R'=benzyl. This solution was stirred at 20° for 1.5 hr and then evaporated. The residue was dissolved in methylene chloride, and this solution was washed with water, dried and evaporated. The 42 mg of material thus obtained was chromatographed on silica gel. Elution with graded mixtures of petroleum ether and ethyl acetate afforded 7 mg of material with the 1:1 mixture. This material crystallized when triturated with ether. Recrystallization from methylene chloride-petroleum ether afforded 2-isopropenyl-2-benzyloxycarbonyl-5-phenylacetamido-5,6-dehydrooxazine-4-one, m.p. 162°–163°. The NMR spectrum shows peaks at 8.33 (1H, s), 7.53 (10H, s), 5.50 (4H, br, s), 3.93 (2H, s), 1.98 (3H, s). The IR spectrum shows carbonyl absorptions at 1725, 1690 and 1642 cm$^{-1}$.

An alternative mode of cyclization of this mixture XXII and XXIII in which R=R'=benzyl, makes use of the procedure of Example 8 to form the epimeric 2-bromomethyl-2-methyl-3R-benzyloxycarbonyl-6S-phenylacetamido-1-oxa-4-aza-5R-bicyclo[3,2,0]heptane-7-ones.

I claim:

1. The CIS compound of the formula:

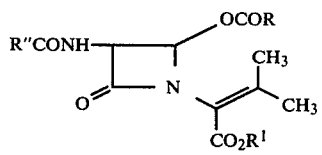

wherein R stand for loweralkyl

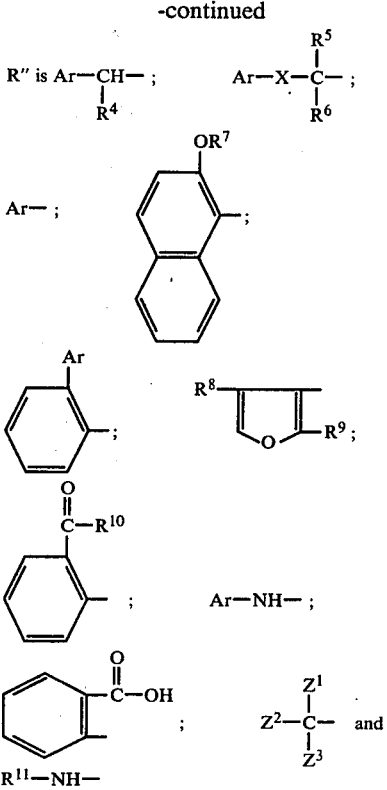

wherein R$^4$ represents a member selected from the group consisting of hydrogen, amino, carbobenzoxyamino, phenyl, fluoro, chloro, bromo, iodo, and (lower)-alkoxy; X represents a member selected from the group consisting of oxygen and sulfur; R$^5$ and R$^6$ each represent a member selected from the group consisting of hydrogen, phenyl, benzyl, phenethyl and (lower)alkyl; R$^7$ represents (lower)alkyl; R$^8$ and R$^9$ each represent a member selected from the group consisting of (lower)alkyl, (lower)alkylthio, benzylthio, cyclohexyl, cyclopentyl, cycloheptyl, benzyl, phenethyl, phenylpropyl, furyl, thienyl, naphthyl and Ar—; R$^{10}$ represents a member selected from the group consisting of (lower)alkylamino, di(lower)alkylamino, cycloalkylamino having from 3 to 7 carbon atoms inclusive, allylamino, diallylamino, phenyl(lower)-alkylamino, morpholino, (lower)alkylmorpholino, di(lower)-alkylmorpholino, morpholino(lower)alkylamino, pyrrolidino, (lower) alkylpyrrlidino, di(lower)alkylpyrrolidino, N,N-hexamethyleneimino, piperidino, (lower)alkylpiperidino, di(lower)-alkylpiperidino, 1,2,5,6-tetrahydropyridino, N-(lower)-alkylpiperazino, N-phenylpiperazino, N-(lower)alkyl(lower)-alkylpiperazino, N-(lower)-alkyl-di(lower)alkylpiperazino, furfurylamino, tetrahydrofurfurylamino, N-(lower)alkyl-N-furfurylamino, N-alkyl-N-anilino and (lower)alkoxyanilino; $Z^1$, $Z^2$ and $Z^3$ each represent a member selected from the group consisting of (lower)alkyl and Ar—; $R^{11}$ represents a member selected from the group consisting of (lower)alkyl, (lower)-cycloalkyl, naphthyl, benzyl, phenethyl and

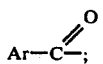

and Ar— represents a monovalent radical having one of the formulae:

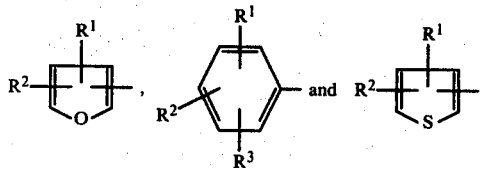

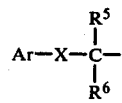

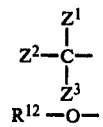

wherein Ar is a monovalent radical selected from

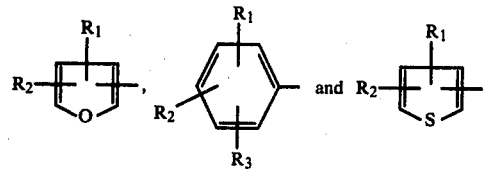

wherein
- $R_1$, $R_2$ and $R_3$ are each a member selected from hydrogen, chloro, bromo, iodo, trifluoromethyl, phenyl, loweralkyl and loweralkoxy, but only one of said $R_1$, $R_2$ and $R_3$ may represent phenyl;
- ($R^4$ is hydrogen, amino, carbobenzoxyamino, phenyl, fluoro, chloro, bromo, iodo, and loweralkoxy;
- X is oxygen or sulfur;
- $R^5$ and $R^6$ are hydrogen, phenyl, benzyl, phenethyl and loweralkyl;
- $Z^1$, $Z^2$ and $Z^3$ stand for loweralkyl or the Ar—group;
- $R^{12}$ is 2,2,2-trichloroethyl or benzyl;
- $R^1$ is hydrogen, loweralkyl, benzyl, benzhydryl, loweralkoxybenzyl, or 2,2,2-trichloroethyl; and
wherein $R^1$, $R^2$ and $R^3$ are each a member selected from the group consisting of hydrogen, chloro, bromo, iodo, trifluoromethyl, phenyl, (lower)alkyl and (llower)alkoxy, but only one of the groups $R^1$, $R^2$ and $R^3$ may represent phenyl.

2. The compound of claim 1 which is methyl 2-(2'R-phenylacetoxy-3'S-phenylcarboxamido-4'-oxo)azetidinyl-3-methyl-2-butenoate.

* * * * *